US00PP21127P2

(12) United States Plant Patent
van Kleinwee

(10) Patent No.: US PP21,127 P2
(45) Date of Patent: Jun. 29, 2010

(54) ***LOBELIA* PLANT NAMED 'LOPLIPW08'**

(50) Latin Name: *Lobelia erinus*
Varietal Denomination: Loplipw08

(75) Inventor: Theodorus Cornelis Maria van Kleinwee, Zwaag (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/454,789

(22) Filed: May 22, 2009

(51) Int. Cl.
*A01H 5/00* (2006.01)

(52) U.S. Cl. ..... Plt./451

(58) Field of Classification Search ..... Plt./263, Plt./451
See application file for complete search history.

*Primary Examiner*—Susan B McCormick Ewoldt
(74) *Attorney, Agent, or Firm*—S. Matthew Edwards

(57) ABSTRACT

A new *Lobelia* plant named "Loplipw08,' particularly distinguished by the spreading to upright plant habit, medium vigor, early flowering and purple-violet flower color.

1 Drawing Sheet

Latin name of the genus and species of the plant claimed: *Lobelia erinus.*

Varietal denomination: 'Loplipw08'.

BACKGROUND OF THE NEW PLANT

The present invention comprises a new *Lobelia*, botanically known as *Lobelia erinus,* and hereinafter referred to by the variety name 'Loplipw08.'

'Loplipw08' is a product of a planned breeding program. The new cultivar 'Loplipw08' has spreading to upright plant habit, medium vigor, early flowering and purple-violet flower color.

'Loplipw08' originated from a hybridization in a controlled breeding program in Enkhuizen, Netherlands. The female parent was an unpatented hybrid seedling identified as 'E0055-1' with pink flowers. 'E0055-1' has smaller flowers, a more upright habit and is less floriferous than 'Loplipw08.'

The male parent of 'Loplipw08' was an unpatented hybrid seedling identified as 'D0044-1' with bluish-purple color. 'D0044-1' has more vigor and lighter green foliage than 'Loplipw08.'

'Loplipw08' was selected as a single flowering plant within the progeny of the stated cross in May, 2004 in a controlled environment in Enkhuizen, Netherlands. The pollination took place in July 2003, the seed sown in March 2004.

The first act of asexual reproduction of 'Loplipw08' was accomplished when vegetative cuttings were taken from the initial selection in June 2004 in a controlled environment in Enkhuizen, Netherlands.

Horticultural examination of plants grown from cuttings of the plant initiated in June 2004 in Enkhuizen, Netherlands, and continuing thereafter, has demonstrated that the combination of characteristics as herein disclosed for 'Loplipw08' are firmly fixed and are retained through successive generations of asexual reproduction.

'Loplipw08' has not been observed under all possible environmental conditions. The phenotype may vary significantly with variations in environment such as temperature, light intensity and day length.

A Plant Breeder's Right for this cultivar was applied for in the Community Plant Variety Office on Apr. 22, 2008.

'Loplipw08' has not been made publicly available more than one year prior to the filing of this application.

BRIEF DESCRIPTION OF THE NEW VARIETY

The accompanying photographic drawing shows typical flower and foliage characteristics of 'Loplipw08' with colors being as true as possible with an illustration of this type. The photographic drawing shows a flowering potted plant of the new variety.

DETAILED BOTANICAL DESCRIPTION

The measurements were taken in Enkhuizen, Netherlands, in July 2008 on plants that were growing in field trials. These plants were approximately 22 weeks old.

Color Chart used: Royal Horticultural Society Colour Chart (R.H.S.) 2001

BRIEF SUMMARY OF INVENTION

The following observations, measurements, and comparisons describe plants grown outside in Enkhuizen, Netherlands. The following traits have been repeatedly observed and are determined to be basic characteristics of the new variety. The combination of these characteristics distinguishes this *Lobelia* as a new and distinct variety.

TABLE 1

DIFFERENCES BETWEEN THE NEW VARIETY 'LOBLIPW08' AND A SIMILAR VARIETY

| | 'Loblipw08' | 'Loblilaca' (U.S. Plant Pat. No. 17,722) |
|---|---|---|
| Vigor | Medium | Very vigorous |
| Flower color | N82C | 80A |
| Flowering response | Earlier | Later |

Plant:

*Form, growth and habit.*—Spreading to upright, freely branching with lateral branching at every node. Pinching will enhance branching. Branches are strong and flexible.

*Plant height.*—25 cm.
*Plant width.*—35 cm.
*Root description.*—Fibrous and freely branching.

Foliage:
*Type.*—Alternate.
*Immature, leaf color, upper surface.*—RHS 144A.
*Lower surface.*—RHS 144A.
*Mature, leaf color, upper surface.*—RHS 137A.
*Lower surface.*—RHS 137C.
*Length.*—1.0-3.0 cm.
*Width.*—Up to 2.0 cm.
*Shape.*—Ligulate to falcate.
*Base shape.*—Attenuate.
*Apex shape.*—Rounded.
*Margin.*—Entire to occasionally dentate.
*Texture.*—Smooth.
*Venation.*—Pinnate.
*Color of veins, upper surface.*—RHS 137A.
*Color of veins, lower surface.*—RHS 137C.

Stem:
*Color of stem.*—RHS 146B.
*Length of stem.*—Approximately 20-24 cm.
*Diameter.*—0.2-0.25 cm.
*Length of internodes.*—1-3 cm.
*Texture.*—Pubescent.
*Color of peduncle.*—RHS 146B.
*Length of peduncle.*—2 cm.
*Peduncle diameter.*—Less than 0.1 cm.
*Texture.*—Pubescent.

Inflorescence:
*Type.*—Flowers at apical axils, usually one flower per axil. Flowers labiate, upper lip consisting of two small petals and lower lip consisting of three larger and broader petals. Flowers face outward and are freely and continuously flowering.
*Lastingness on plant.*—10-14 days depending on temperature.
*Number of flowers per plant.*—120-160.

BUD (just before opening):
*Color.*—RHS 82D.
*Length.*—0.9 cm.
*Width.*—0.2-0.3 cm.
*Shape.*—Tubular.
*Depth of flower.*—1.6 cm.
*Diameter of flower.*—1.4 cm.
*Color upper petals, upper surface.*—RHS N82C, basal marking of RHS N82A.
*Color upper petals, lower surface.*—RHS N82D.
*Length of upper petals.*—0.5 cm.
*Width of upper petals.*—0.2 cm.
*Color lower petals, upper surface.*—RHS N82C, near base marking of RHS N82A and basal white spot of RHS N155A.
*Color lower petals, lower surface.*—RHS N82D.
*Length of lower petals.*—0.8 cm.
*Width of lower petals.*—0.3-0.8 cm.
*Petal shape.*—Obovate.
*Apex shape.*—Mucronulate.
*Margin.*—Entire.
*Petal texture.*—Smooth, upper surface is slightly pubescent.
*Throat.*—Color: RHS N87C. Diameter: 0.1 cm. Depth: 0.6 cm. Texture: Pubescent. Number of sepals: Five, fused at base. Color of sepals: RHS 146B both surfaces. Length of sepals: 0.6 cm. Width of sepals: 0.1 cm. Sepal shape: Ligulate. Apex shape: Acute. Margins: Entire. Texture: Smooth.

Reproductive organs:
*Pistils, quantity per flower.*—One.
*Pistil length.*—0.6 cm.
*Pistil width.*—Less than 0.1 cm.
*Style color.*—RHS 134D.
*Stigma color.*—RHS 83A.
*Stigma shape.*—Tri-lobed.
*Ovary color.*—RHS 144A.
*Stamens, quantity per flower.*—Five.
*Anther color.*—RHS 198A.
*Anther shape.*—Oblong.
*Anther length.*—0.2 cm.
*Pollen color.*—Lighter than RHS 4D.
*Pollen amount.*—Slight.

Seed and fruit development: Some seed and fruit development has been observed on plants of the new *Lobelia*.
*Seed* (*when mature*).—Color: RHS 165A. Shape: Ovate. Diameter: 0.3 cm. Length: 0.2 cm.
*Fruit* (*when ripened*).—Color: 199B. Diameter: 0.3 cm. Length: 0.6 cm. Number of seeds per fruit: 200-300.

Disease/pest resistance: Plants of the new *Lobelia* have not been noted to be resistant to pathogens and pests common to *Lobelia*.

Garden performance: Plants of the new *Lobelia* have been observed to have a rather good garden performance. Plants of the new *Lobelia* have been noted to tolerate rain, wind, and temperatures from 7° C. to 30° C.

What is claimed is:

1. A new and distinct variety of *Lobelia* plant named "Loplipw08,' substantially as illustrated and described herein.

* * * * *

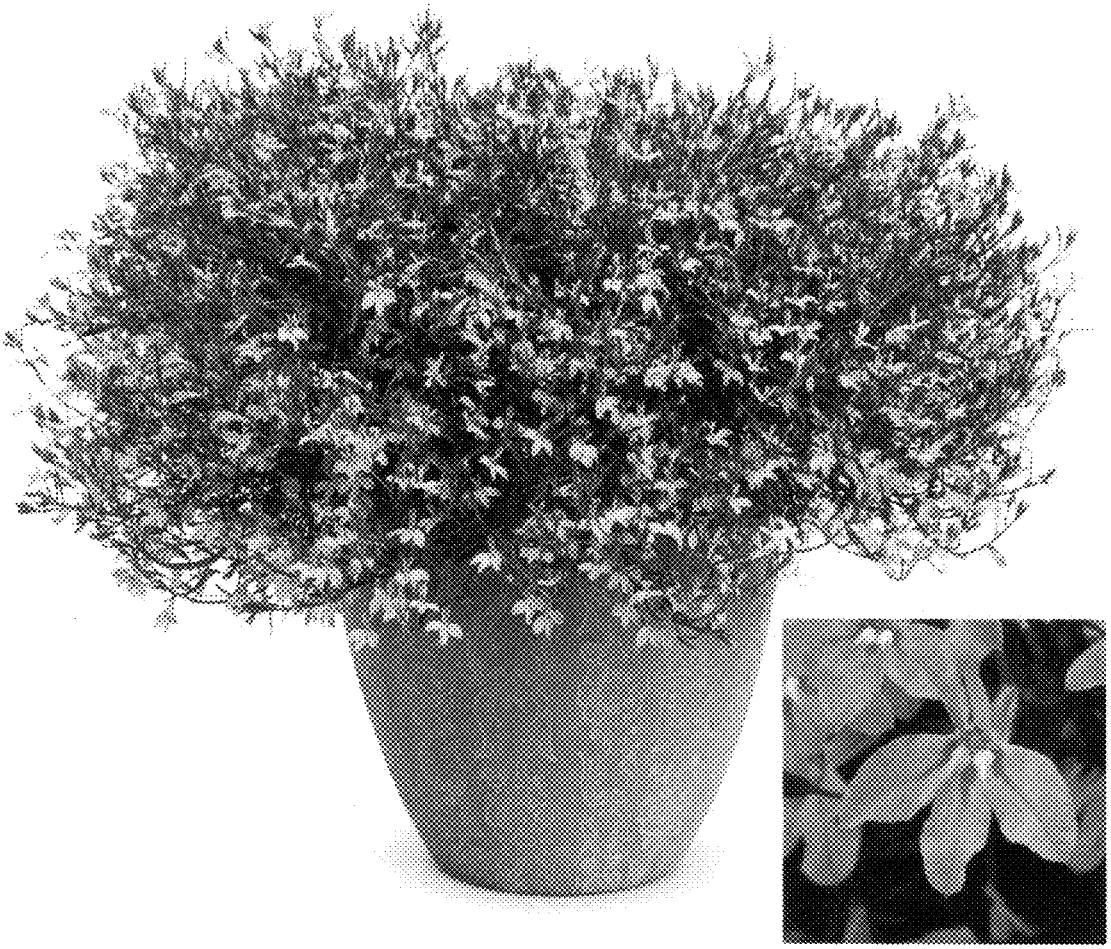

UNITED STATES PATENT AND TRADEMARK OFFICE

CERTIFICATE OF CORRECTION

PATENT NO. : PP 21,127 P2
APPLICATION NO. : 12/454789
DATED : June 29, 2010
INVENTOR(S) : van Kleinwee It is certified that error appears in the above-identified patent and that said Letters Patent is hereby corrected as shown below:

In the title page, at Item (54), delete "'LOPLIPW08'" and insert therefor --'LOBLIPW08'--

In the title page, In the Varietal denomination, at Item (50), delete "'Loplipw08'" and insert therefor --'Loblipw08'--

In the title page, In the ABSTRACT, at Item (57), delete "'Loplipw08'" and insert therefor --'Loblipw08'--

At column 1, at line 3, delete "'Loplipw08'" and insert therefor --'Loblipw08'--

At column 1, at lines 9, 10, and 11, delete "'Loplipw08'" and insert therefor --'Loblipw08'--

At column 1, at line 14, delete "'Loplipw08'" and insert therefor --'Loblipw08'--

At column 1, at lines 18 and 19, delete "'Loplipw08'" and insert therefor --'Loblipw08'--

At column 1, at lines 22 and 23, delete "'Loplipw08'" and insert therefor --'Loblipw08'--

At column 1, at line 27, delete "'Loplipw08'" and insert therefor --'Loblipw08'--

At column 1, at line 34, delete "'Loplipw08'" and insert therefor --'Loblipw08'--

At column 1, at line 37, delete "'Loplipw08'" and insert therefor --'Loblipw08'--

At column 2, at line 1, delete "'Loplipw08'" and insert therefor --'Loblipw08'--

At column 2, at line 7, delete "'Loplipw08'" and insert therefor --'Loblipw08'--

At column 2, in TABLE 1, at line 31, delete "'Loplipw08'" and insert therefor --'Loblipw08'--

Signed and Sealed this

Thirty-first Day of August, 2010

David J. Kappos

David J. Kappos
*Director of the United States Patent and Trademark Office*

At column 2, in TABLE 1, at line 34, delete "'Loplipw08'" and insert therefor --'Loblipw08'--

At column 4, in claim 1, at line 48, delete "'Loplipw08'" and insert therefor --'Loblipw08'--